United States Patent
Hoshi et al.

(10) Patent No.: US 9,265,270 B2
(45) Date of Patent: Feb. 23, 2016

(54) LACTOBACILLUS CULTURE AND METHOD FOR PRODUCING SAME

(71) Applicant: KABUSHIKI KAISHA YAKULT HONSHA, Minato-ku (JP)

(72) Inventors: Ryotaro Hoshi, Tokyo (JP); Akihisa Matsui, Tokyo (JP); Takao Suzuki, Tokyo (JP)

(73) Assignee: Kabushiki Kaisha Yakult Honsha, Minato-ku (JP)

(*) Notice: Subject to any disclaimer, the term of this patent is extended or adjusted under 35 U.S.C. 154(b) by 0 days.

(21) Appl. No.: 14/388,655

(22) PCT Filed: Mar. 27, 2013

(86) PCT No.: PCT/JP2013/058911
§ 371 (c)(1),
(2) Date: Sep. 26, 2014

(87) PCT Pub. No.: WO2013/146836
PCT Pub. Date: Oct. 3, 2013

(65) Prior Publication Data
US 2015/0056683 A1 Feb. 26, 2015

(30) Foreign Application Priority Data
Mar. 27, 2012 (JP) .................. 2012-070473

(51) Int. Cl.
*C12N 1/20* (2006.01)
*A23C 9/123* (2006.01)
*C12N 1/38* (2006.01)

(52) U.S. Cl.
CPC ............... *A23C 9/1234* (2013.01); *C12N 1/20* (2013.01); *C12N 1/38* (2013.01); *A23C 2240/15* (2013.01); *A23Y 2220/17* (2013.01); *A23Y 2220/37* (2013.01)

(58) Field of Classification Search
None
See application file for complete search history.

(56) References Cited

U.S. PATENT DOCUMENTS

2008/0292751 A1* 11/2008 Ogasawara et al. ............. 426/43
2010/0015281 A1*  1/2010 Hoshi et al. .................... 426/43
2013/0209412 A1*  8/2013 Hoshi et al. ................. 424/93.4

FOREIGN PATENT DOCUMENTS

| CA | 2609458 | * 11/2006 |
| JP | 08-116872 | 5/1996 |
| JP | 2000-197468 | 7/2000 |
| JP | 2012-75382 A | 4/2012 |
| WO | 2006/126476 | 11/2006 |
| WO | 2006/129508 | 12/2006 |
| WO | 2012/043532 | 4/2012 |

OTHER PUBLICATIONS

International Search Report issued May 14, 2013, in PCT/JP13/058911, filed Mar. 27, 2013.
Office Action issued Jan. 6, 2015 in Japanese Patent Application No. 2012-070473.

* cited by examiner

*Primary Examiner* — Ralph Gitomer
(74) *Attorney, Agent, or Firm* — Oblon, McClelland, Maier & Neustadt, L.L.P.

(57) ABSTRACT

An object of the present invention is to provide a technique for improving a taste derived from *Rubus suavissimus* S. Lee (Rosaceae) while maintaining the effect of extracts of *Rubus suavissimus* S. Lee (Rosaceae) to enhance the proliferative capability or viability in culturing of lactic acid bacteria. Provided is a lactic acid bacteria culture product which is obtained by culturing a lactic acid bacterium in a culture medium, wherein the culture medium contains an essence of *Rubus suavissimus* S. Lee (Rosaceae), wherein the essence of *Rubus suavissimus* S. Lee (Rosaceae) is a concentrate obtained through an electrodialysis of a mixture obtained by adding an inorganic salt to an extract of *Rubus suavissimus* S. Lee (Rosaceae).

14 Claims, No Drawings

LACTOBACILLUS CULTURE AND METHOD FOR PRODUCING SAME

This application is a National Stage application filed under Rule 371 based upon PCT/JP2013/058911 filed Mar. 27, 2013.

TECHNICAL FIELD

The present invention relates to a lactic acid bacteria culture product which is obtained by culturing a lactic acid bacterium, as well as a method of producing the same.

BACKGROUND ART

Culturing of lactic acid bacteria has been conducted in various manners, and is most often carried out by using animal milk as a culture medium for production of lactic acid bacteria formulations or production of fermented milk, lactic acid bacteria beverages, cheese and the like. However, since, in general, nutritional requirements of lactic acid bacteria vary among species, some lactic acid bacteria may not sufficiently grow in a culture medium consisting only of animal milk. Further, even when bacterial strains exhibiting a relatively higher proliferation activity are used in such a culture medium consisting only of animal milk, it is required to carry out culturing of the bacteria for several days in order to obtain fermented products having a sufficient acid level in producing fermented milk, lactic acid bacteria beverages and the like.

However, since culturing of lactic acid bacteria over a long period of time causes a reduction in the viable cell count, such a culturing technique is not always considered as a favorable culturing method for production of lactic acid bacteria beverages, fermented milk and the like for which various physiological effects are expected and for which viable cell counts are considered important.

Furthermore, for production of various beverages or foods in which flavors of fermented products obtained by culturing lactic acid bacteria are considered critical, bacterial strains used therein cannot be selected only from a viewpoint of their proliferative capacities. Consequently, there are cases where lactic acid bacteria providing fermented products having good tastes are selected and used, even if their proliferative capacities are inferior.

Therefore, in culturing of lactic acid bacteria, it is an ordinary technique that various growth-promoting substances are preliminary added to culture media in order to improve the culturing efficiencies, and such a technique has been well-known. In general, as examples of those which have been considered effective as growth-promoting substances, *chlorella* extracts, iron salts, vitamins, protein digests containing amino acids or peptides, yeast extracts, and the like can be mentioned.

The present Applicant has also reported that an extract of *Rubus suavissimus* S. Lee (Rosaceae) or the like are added to culture media in order to enhance the proliferative capabilities or survivability in culturing of lactic acid bacteria Patent Document 1.

However, in products such as fermented milk in which an extract of *Rubus suavissimus* S. Lee (Rosaceae) has been added, while the proliferative capability or survivability of lactic acid bacteria could be enhanced, the products had bitterness which is derived from the *Rubus suavissimus* S. Lee (Rosaceae), and therefore, had a problem in their tastes.

CITATION LIST

Patent Document

Patent Document 1: WO2006/126476

SUMMARY OF INVENTION

Technical Problem

Accordingly, an object of the present invention is to provide a technique for improving the tastes of the products while maintaining the effect of an extract of *Rubus suavissimus* S. Lee (Rosaceae) to enhance the proliferative capability or survivability of lactic acid bacteria in culturing thereof.

Solution to Problem

The present invention relates to a lactic acid bacteria culture product which is obtained by culturing a lactic acid bacterium in a culture medium, wherein the culture medium contains an essence of *Rubus suavissimus* S. Lee (Rosaceae) which is a concentrate obtained through an electrodialysis of a mixture obtained by adding an inorganic salt to an extract of *Rubus suavissimus* S. Lee (Rosaceae).

Moreover, the present invention relates to a method of producing a lactic acid bacteria culture product, the method including: blending an essence of *Rubus suavissimus* S. Lee (Rosaceae) into a culture medium at an arbitrary stage in production of the lactic acid bacteria culture product which is obtained by culturing a lactic acid bacterium in the culture medium, wherein the essence of *Rubus suavissimus* S. Lee (Rosaceae) is a concentrate obtained through an electrodialysis of a mixture obtained by adding an inorganic salt to an extract of *Rubus suavissimus* S. Lee (Rosaceae).

Furthermore, the present invention relates to a method for promoting growth of a lactic acid bacterium, the method including: blending an essence of *Rubus suavissimus* S. Lee (Rosaceae) into a culture medium, wherein the essence of *Rubus suavissimus* S. Lee (Rosaceae) is a concentrate obtained through an electrodialysis of a mixture obtained by adding an inorganic salt to an extract of *Rubus suavissimus* S. Lee (Rosaceae); and culturing the lactic acid bacterium in the culture medium.

Advantageous Effects of Invention

In the lactic acid bacteria culture product according to the present invention, the proliferative capability and the survivability of lactic acid bacteria are enhanced since an essence of *Rubus suavissimus* S. Lee (Rosaceae), which is a concentrate obtained through electrodialysis of a mixture obtained by adding an inorganic salt to an extract of *Rubus suavissimus* S. Lee (Rosaceae), has been added thereto during culturing of lactic acid bacteria. Consequently, the viable cell count in the culture product is higher, while such a higher viable cell count will be maintained, and also, the culture product has no bitterness derived from the *Rubus suavissimus* S. Lee (Rosaceae), and therefore, has a better taste.

Accordingly, the lactic acid bacteria culture product according to the present invention has no problem in its taste, and can be utilized for various fermented dairy products. Further, in such fermented dairy products, deterioration of tastes or reductions in the viable cell counts hardly occur during storage, and therefore, the fermented dairy products are highly valuable and are useful in improving health.

DESCRIPTION OF EMBODIMENTS

The lactic acid bacteria culture product of the present invention is obtained by culturing a lactic acid bacterium in a culture medium wherein the culture medium contains an essence of *Rubus suavissimus* S. Lee (Rosaceae), wherein the essence of *Rubus suavissimus* S. Lee (Rosaceae) is a concentrate obtained through an electrodialysis of a mixture obtained by adding an inorganic salt to an extract of *Rubus suavissimus* S. Lee (Rosaceae).

The essence of *Rubus suavissimus* S. Lee (Rosaceae) which is used for obtaining the above-mentioned lactic acid bacteria culture product and which is a concentrate obtained through an electrodialysis of a mixture obtained by adding an inorganic salt to an extract of *Rubus suavissimus* S. Lee (Rosaceae) can be obtained in the following way. At first, leaves or stems (preferably leaves) of *Rubus suavissimus* S. Lee (Rosaceae) belonging to the genus *Rubus* in the family Rosaceae are subjected to a solvent extraction without any treatment, or are subjected to treatments such as washing, peeling, drying, and crushing, if desired, and then, are subjected to a solvent extraction, thereby obtaining the extract of *Rubus suavissimus* S. Lee (Rosaceae).

The solvent used for production of the above extract of *Rubus suavissimus* S. Lee (Rosaceae) is not particularly limited, and, for example, water, or organic solvents such as $C_1$-$C_5$ lower alcohols (e.g. ethanol), ethyl acetate, glycerin, and propylene glycol can be mentioned. These solvents may be used singularly, or two or more of the solvents may be mixed. Among these solvents, water or aqueous solvents such as water/lower alcohols are particularly preferable.

Moreover, an extraction method for the extract of *Rubus suavissimus* S. Lee (Rosaceae) using the above-described solvent is not particularly limited, and, for example, the acid extraction method is preferable. Additionally, the acid extraction process is preferably carried out under an acidic condition of a pH of 4.0 or lower, more preferably of a pH of 3.0 to 4.0. For the acid component used for adjusting the pH of the solvent in carrying out the acid extraction, any substance can be used without particular limitations as long as the substance is acidic. As preferable examples thereof, organic acids such as citric acid, malic acid, tartaric acid, succinic acid, lactic acid and acetic acid can be mentioned.

Furthermore, conditions for the extraction of the extract of *Rubus suavissimus* S. Lee (Rosaceae) using the above-described solvent are not particularly limited, and, for example, it is preferable that the extraction treatment be carried out at a temperature of 0° C. to 100° C. (more preferably 10° C. to 40° C.) for about 30 to 60 minutes.

The extract of *Rubus suavissimus* S. Lee (Rosaceae) obtained in this way is subjected to filtration, centrifugation and the like, if desired, and then, an inorganic salt is added thereto, followed by subjecting the resulting mixture to an electrodialysis.

The inorganic salt added to the extract of *Rubus suavissimus* S. Lee (Rosaceae) is not particularly limited as long as it is a salt formed of an inorganic acid and an inorganic base. For example, one or more selected from a potassium salt such as potassium chloride, a sodium salt such as sodium chloride, a calcium salt such as calcium chloride, and a magnesium salt such as magnesium chloride can be mentioned. Among these inorganic salts, a magnesium salt is preferable, and magnesium chloride is more preferable. The amount of the inorganic salt added to the extract of *Rubus suavissimus* S. Lee (Rosaceae) is not particularly limited, but 0.01 to 0.5 mol/L is preferable, and 0.02 to 0.2 mol/L is more preferable, in terms of anhydride. These inorganic salts may be either hydrates or anhydrides.

With regard to an electrodialyzer used for the electrodialysis, for example, an electrodialyzer in which a region between a cathode and an anode is partitioned alternately with a plurality of cationic-exchange membranes and a plurality of anionic-exchange membranes, and thus, a cathode chamber, an anode chamber, a plurality of desalting chambers, and a plurality of concentrating chambers are provided can be mentioned. In such an electrodialyzer, a concentrate solution in which ionic substances are concentrated, and a desalted solution in which ionic substances have been removed are obtained. That is, regions which are each partitioned with the cationic-exchange membranes each located on the side where the cathode is present and the anionic-exchange membranes each located on the opposite side where the anode is present correspond to the concentrating chambers, and each liquid which refluxes in each concentrating chamber corresponds to the concentrate solution. Further, regions which are each partitioned with the anionic-exchange membranes each located on the side where the cathode is present and the cationic-exchange membranes each located on the opposite side where the anode is present correspond to the desalting chambers, and each liquid which refluxes in each desalting chamber corresponds to the desalted solution. Electrodialyzers are commercially-available, for example, as trade names of "ACILYZER" (ASTOM Corporation) and the like, and such commercially-available electrodialyzers can also be utilized.

The above-described essence of *Rubus suavissimus* S. Lee (Rosaceae) can be obtained in the following way. That is, the extract of *Rubus suavissimus* S. Lee (Rosaceae) to which an inorganic salt has been added is refluxed in a desalting chamber in an electrodialyzer, while water or the like is refluxed in a concentrating chamber, to carryout the electrodialysis treatment, and the resulting concentrate is collected as the essence of *Rubus suavissimus* S. Lee (Rosaceae). Conditions for the electrodialysis are not particularly limited. For example, a method can be mentioned, in which, while an amount of water equivalent to 5% to 50% (preferably 10% to 30%) by mass (hereinafter, simply referred to as "%") of the extract of *Rubus suavissimus* S. Lee (Rosaceae) is refluxed in the concentrating chamber, a voltage of 10 to 200 V, preferably 50 to 100 V is applied to the region between the anode and the cathode, and an electric current of 10 to 200 A, preferably to 100 A is passed through the region to carry out the electrodialysis treatment until the electric conductivity in the desalting chamber reaches equilibrium (2 millisiemens per centimeter (mS/cm)), and then, a concentrate is collected to obtain the essence of *Rubus suavissimus* S. Lee (Rosaceae). For the liquid which is refluxed in the concentrating chamber, beside water, for example, an electrolyte solution such as a brine solution or a citric acid aqueous solution can also be used.

As to the essence of *Rubus suavissimus* S. Lee (Rosaceae) obtained in the above-described way, the essence directly obtained from the electrodialysis as it is can be used; or the resulting essence of *Rubus suavissimus* S. Lee (Rosaceae) may be subjected to a purification/concentration process by ultrafiltration, centrifugation or the like, and the purified/concentrated product thus obtained may be used. Alternatively, the purified/concentrated product may be further dried by means of spray drying, freeze drying or the like, and the powdery product thus obtained may be used.

The amount of the above-described essence of *Rubus suavissimus* S. Lee (Rosaceae) added to the culture medium in which lactic acid bacteria can grow is not particularly limited.

For example, as for an essence of *Rubus suavissimus* S. Lee (Rosaceae) exhibiting a Brix of 12, the concentration of the essence in the culture medium is 0.01% to 1.0%, preferably 0.01% to 0.5%, more preferably 0.02% to 0.2%. The Brix refers to a value measured with a digital refractometer such as "RX-7000α" (ATAGO CO., LTD.).

Moreover, as to when to add the above-described essence of *Rubus suavissimus* S. Lee (Rosaceae) to the culture medium, it is preferable that the essence be added thereto before fermenting the lactic acid bacterium. However, the time of addition is not limited to such timing, and the essence may be added to the culture medium even during fermentation of the lactic acid bacterium or after completion of fermentation of the lactic acid bacterium. Additionally, the essence can also be added to the culture medium more than once. In particular, addition of the essence of *Rubus suavissimus* S. Lee (Rosaceae) to the culture medium before the fermentation of the lactic acid bacterium is preferable because the cell count and the survivability after completion of the culturing can be maintained at a higher level.

Furthermore, as to the culture medium to which the above-described essence of *Rubus suavissimus* S. Lee (Rosaceae) is added, animal milk culture media which include raw milk (e.g. bovine milk, goat milk, horse milk, and sheep milk) or dairy products (e.g. powdered skim milk, whole powdered milk, and fresh cream); liquid milk derived from plants (e.g. soy milk); or various synthetic culture media can be mentioned. Additionally, ingredients which are used in general culture media for lactic acid bacteria can be added to the above-mentioned culture media. As examples of such ingredients, vitamins such as vitamin A, B-complex vitamins, vitamin C and vitamin E, various peptides, amino acids, salts of calcium, magnesium and the like can be mentioned.

Additionally, oleic acid or derivatives thereof may be added to the above-described culture media. As examples of such oleic acid or derivatives thereof, oleic acid, or derivatives of oleic acid such as salts of oleic acid (e.g. sodium oleate, potassium oleate), and oleic acid esters such as glycerin-oleic acid esters, polyglycerin-oleic acid esters or sucrose-oleic acid esters can be mentioned. Oleic acid or derivatives thereof may be added to the culture media to a final concentration of about 5 to 50 ppm, preferably 5 to 25 ppm in terms of oleic acid.

The lactic acid bacterium which is cultured in order to obtain the lactic acid bacteria fermented product of the present invention is not particularly limited as long as it is a lactic acid bacterium generally used for food manufacturing. For example, a bacterium belonging to the genus *Lactobacillus* (e.g. *Lactobacillus casei, Lactobacillus gasseri, Lactobacillus acidophilus, Lactobacillus cremoris, Lactobacillus helveticus, Lactobacillus salivarius, Lactobacillus fermentum, Lactobacillus yoghurti, Lactobacillus delbrueckii* subsp. *bulgaricus, Lactobacillus delbrueckii* subsp. *delbrueckii,* and *Lactobacillus johnsonii*); a bacterium belonging to the genus *Streptococcus* (e.g. *Streptococcus thermophiles*); a bacterium belonging to the genus *Lactococcus* (e.g. *Lactococcus lactis* subsp. *lactis, Lactococcus lactis* subsp. *cremoris, Lactococcus plantarum,* and *Lactococcus raffinolactis*); and a bacterium belonging to the genus *Enterococcus* (e.g. *Enterococcus faecalis,* and *Enterococcus faecium*) can be mentioned. Among these lactic acid bacteria, one or more lactic acid bacteria selected from the group consisting of a bacterium belonging to the genus *Lactobacillus*, a bacterium belonging to the genus *Streptococcus*, and a bacterium belonging to the genus *Lactococcus* are preferable. Among them, *Lactobacillus casei* or *Lactobacillus gasseri* is preferable, and, *Lactobacillus casei* YIT9029 (FERM BP-1366; the date of receipt: Jan. 12, 1981; the International Patent Organism Depositary, the National Institute of Technology and Evaluation (Tsukuba Central 6, 1-1, Higashi 1-chome, Tsukuba-shi, Ibaraki-ken, 305-8566, JAPAN)) is particularly preferable. The lactic acid bacterium (bacteria) in the present invention refers to a lactic acid bacterium which is a facultative anaerobic bacterium, and therefore, does not include a bacterium belonging to the genus *Biffidobacterium* which is an obligate anaerobic bacterium.

Conditions for culturing the lactic acid bacterium to obtain the lactic acid bacteria fermented product of the present invention are not particularly limited. For example, conditions in which the lactic acid bacterium is inoculated into the culture medium such that the bacterial count in the culture medium is about $1.0 \times 10^3$ to $1.0 \times 10^9$ cfu/mL, and then, the lactic acid bacterium is cultured at about 30° C. to 40° C. for about 1 to 7 days can be mentioned. Additionally, as to the culturing condition in this case, a technique which is suitable for culturing a lactic acid bacterium used therein can be appropriately selected from static culture, stirring culture, shaking culture, aeration culture and the like to carry out culturing of the lactic acid bacterium.

The lactic acid bacteria fermented product obtained in this way will exhibit a higher viable cell count, and will maintain such a higher viable cell count, while having no bitterness derived from *Rubus suavissimus* S. Lee (Rosaceae) and having a better taste. Then, the lactic acid bacteria fermented product can be utilized alone as a fermented dairy product, or may be mixed with other auxiliary materials which are allowed to be added to general fermented dairy products, to prepare a final fermented dairy product.

In the present invention, the fermented dairy product includes fermented soy milk or fermented milk defined in the Japanese Ministerial Ordinance on Milk and Milk products Concerning Compositional Standards and the like; beverages such as dairy lactic acid bacteria beverages, hard yogurt, soft yogurt, plain yogurt, even kefir, cheese and the like. Additionally, the fermented dairy product of the present invention includes beverages and foods using various lactic acid bacteria, and includes fermented milk, lactic acid bacteria beverages, Kefir, cheese and the like of, for example, a plain type, flavored type, fruit type, sweetened type, soft type, drinkable type, solid (hard) type, or frozen type.

These fermented dairy products can be obtained by mixing, besides sweetening agents such as syrups, other various food materials (e.g. optional ingredients such as various carbohydrates, thickening agents, emulsifying agents, or various vitamins) into the above-described lactic acid bacteria fermented product, as necessary. As examples of such food materials, carbohydrates such as sucrose, glucose, fructose, palatinose, trehalose, lactose, xylose and maltose; sugar alcohols such as sorbitol, xylitol, erythritol, lactitol, palatinit, reduced starch syrup and reduced maltose syrup; high intensity sweeteners such as aspartame, thaumatin, sucralose, acesulfame K and stevia; various thickening (stabilizing) agents such as agar, gelatin, carrageenan, gum guaiac, xanthan gum, pectin, locust bean gum, gellan gum, carboxymethylcellulose, soybean polysaccharides and propylene glycol alginate; emulsifying agents such as sucrose-fatty acid esters, glycerin-fatty acid esters, polyglycerin-fatty acid esters, sorbitan-fatty acid esters and lecithin; milk fats such as cream, butter, and sour cream; acidic ingredients such as citric acid, lactic acid, acetic acid, malic acid, tartaric acid, and gluconic acid; various vitamins such as vitamin A, complex-B vitamins, vitamin C, and vitamin E; minerals such as calcium, magnesium, zinc, iron, and manganese; and flavors such as a yogurt, berry, orange, quince, perilla, citrus, apple, mint, grape, apricot, pear, custard cream, peach, melon, banana, tropical, herb, black tea or coffee flavor can be mentioned.

The fermented dairy product obtained in this way has a better taste, and also, deterioration in the taste and a reduction in the viable cell count hardly occur even during storage. Therefore, the fermented dairy product is highly valuable, and is useful in improving health.

EXAMPLES

Hereinafter, the present invention will be described with reference to Examples. However, the present invention is not to be considered limited to the Examples.

Reference Example 1

Production of an Extract of *Rubus suavissimus* S. Lee (Rosaceae)

Leaves of *Rubus suavissimus* S. Lee (Rosaceae) were subjected to treatments such as crushing, and then, to the treated leaves were added 15 times their volume of water and an amount of citric acid equivalent to 5% of the leaves, the pH was adjusted to 3.8, and an extraction was carried out at 20° C. for 60 minutes. Further, the resulting extraction solution was concentrated by 5 times with an evaporator, thereby obtaining an extract of *Rubus suavissimus* S. Lee (Rosaceae) exhibiting a Brix of 13.

Production Example 1

Production of an Essence of *Rubus suavissimus* S. Lee (Rosaceae) (1)

Magnesium chloride hexahydrate was added to the above extract of *Rubus suavissimus* S. Lee (Rosaceae) obtained through the extraction at 20° C. for 60 minutes to a final concentration of 0.05 mol/L. Then, the resulting solution was charged to desalting chambers in an electrodialyzer (electrodialytic membrane: AC220-50; the product name: Micro Acilyzer-S-3; the equipment manufacturer: ASTOM Corporation), while an amount of water equivalent to 17% of the extract of *Rubus suavissimus* S. Lee (Rosaceae) was charged to concentrating chambers, an electrodialysis treatment was then conducted until the electric conductivity in the desalting chambers reached equilibrium (specifically, until the electric conductivity reached 2 millisiemens per centimeter (mS/cm)), and a concentrate was collected. Further, the concentrate was concentrated by 5 times with an evaporator, thereby obtaining Essence of *Rubus suavissimus* S. Lee (Rosaceae) 1 exhibiting a Brix of 12.

Example 1

Production of a Culture Product (1)

A 10% powdered skim milk solution was used as a base medium, 0.2% of Essence of *Rubus suavissimus* S. Lee (Rosaceae) 1 prepared in Production Example 1 was added to the base medium, and the resulting medium was subjected to a heat sterilization at 100° C. for 15 minutes, thereby preparing a culture medium. 0.1% of a starter of *Lactobacillus casei* (YIT9029) was inoculated into the culture medium (the initial bacterial count: $1.5 \times 10^6$ cfu/mL). The inoculated culture medium was incubated at 37° C. for 24 hours, and then, was cooled to below 10° C., thereby obtaining a culture product.

In addition, for comparison, instead of Essence of *Rubus suavissimus* S. Lee (Rosaceae) 1, 0.2% of the extract of *Rubus suavissimus* S. Lee (Rosaceae) was added to the base medium, thereby obtaining another culture medium, and another culture product was obtained in the same way with this another culture medium.

The values of pH of culture products were measured with a pH meter (HORIBA F-52), and lactic acid bacteria counts were measured with BCP culture media (manufactured by EIKEN CHEMICAL CO., LTD.). Also, acidities of culture products (a titer obtained by taking 9 g of the culture product and by titrating organic acids therein with a 0.1 N solution of sodium hydroxide until the pH reached 8.5; unit: mL) were measured. Furthermore, tastes of the resulting dairy products were evaluated by a panel of three experts based on the evaluation criteria described below, and the results are shown in Table 1.

<Evaluation Criteria on Tastes>

| Scores | Contents |
| --- | --- |
| 5 | No bitterness was sensed. |
| 4 | Little bitterness was sensed. |
| 3 | Slight bitterness was sensed. |
| 2 | Bitterness was sensed. |
| 1 | Strong bitterness was sensed. |

TABLE 1

| Additives | pH values of culture products | Acidities of culture products | Viable cell counts of culture products (cfu/mL) | Taste |
| --- | --- | --- | --- | --- |
| None | 5.40 | 3.7 | $8.3 \times 10^8$ | 5 |
| Extract of *Rubus suavissimus* S. Lee (Rosaceae) | 4.42 | 8.0 | $6.6 \times 10^9$ | 2 |
| Essence of *Rubus suavissimus* S. Lee (Rosaceae) 1 | 4.40 | 8.1 | $6.3 \times 10^9$ | 5 |

As is clear from Table 1, it was recognized that the dairy products, in which the extract of *Rubus suavissimus* S. Lee (Rosaceae) or Essence of *Rubus suavissimus* S. Lee (Rosaceae) 1 has been added, exhibited lower pH values, compared to the dairy product derived from base medium alone, and that higher viable cell counts could be obtained in the dairy products in which the extract of *Rubus suavissimus* S. Lee (Rosaceae) or Essence of *Rubus suavissimus* S. Lee (Rosaceae) 1 has been added. Additionally, it was recognized that the dairy product obtained using Essence of *Rubus suavissimus* S. Lee (Rosaceae) 1 had a very good taste while it had a pH value and a viable cell count almost equivalent to those for the dairy product obtained using the extract of *Rubus suavissimus* S. Lee (Rosaceae).

Production Example 2

Production of an Essence of *Rubus suavissimus* S. Lee (Rosaceae) (2)

Essences of *Rubus suavissimus* S. Lee (Rosaceae) 2 to 5 were produced in the same manner as Production Example 1 except that the same amounts of sodium chloride, potassium chloride, calcium chloride, and tripotassium citrate, respectively, were used instead of magnesium chloride hexahydrate.

Example 2

Production of Culture Products (2)

Culture products (initial bacterial counts: $1.5\times10^6$ cfu/mL) were obtained in the same manner as Example 1 except that the same amounts of Essences of *Rubus suavissimus* S. Lee (Rosaceae) 2 to 5 were used instead of Essence of *Rubus suavissimus* S. Lee (Rosaceae) 1. With respect to these culture products, pH values, acidities, and viable cell counts were measured, and tastes were evaluated in the same manner as Example 1. The results are shown in Table 2.

TABLE 2

| Additives | Inorganic salt or organic salt | pH values of culture products | Acidities of culture products | Viable cell counts of culture products (cfu/mL) | Taste |
|---|---|---|---|---|---|
| None | None | 5.40 | 3.7 | $8.3 \times 10^8$ | 5 |
| Essence of *Rubus suavissimus* S. Lee (Rosaceae) 1 | Magnesium chloride | 4.40 | 8.1 | $6.3 \times 10^9$ | 5 |
| Essence of *Rubus suavissimus* S. Lee (Rosaceae) 2 | Sodium chloride | 5.23 | 3.9 | $1.2 \times 10^9$ | 4 |
| Essence of *Rubus suavissimus* S. Lee (Rosaceae) 3 | Potassium chloride | 5.09 | 4.2 | $2.1 \times 10^9$ | 5 |
| Essence of *Rubus suavissimus* S. Lee (Rosaceae) 4 | Calcium chloride | 4.88 | 6.0 | $5.4 \times 10^9$ | 4 |
| Essence of *Rubus suavissimus* S. Lee (Rosaceae) 5 | Tripotassium citrate | 5.39 | 3.7 | $9.1 \times 10^8$ | 5 |

As is clear from Table 2, it was recognized that the essence of *Rubus suavissimus* S. Lee (Rosaceae) obtained by addition of magnesium chloride was superior in a growth-promoting effect compared with the essences of *Rubus suavissimus* S. Lee (Rosaceae) obtained by addition of other salts. Additionally, only a small growth-promoting effect was recognized in tripotassium citrate which is an organic salt.

Production Example 3

Production of an Essence of *Rubus suavissimus* S. Lee (Rosaceae) (3)

Essences of *Rubus suavissimus* S. Lee (Rosaceae) 6 to 10 were produced in the same manner as Production Example 1 except that 0.01, 0.02, 0.1, 0.2 and 0.5 mol/L, respectively, of magnesium chloride were used instead of 0.05 mol/L of magnesium chloride.

Example 3

Production of Culture Products (3)

Culture products (initial bacterial counts: $1.5\times10^6$ cfu/mL) were obtained in the same manner as Example 1 except that the same amounts of Essences of *Rubus suavissimus* S. Lee (Rosaceae) 6 to 10 produced in Production Example 3 were used instead of Essence of *Rubus suavissimus* S. Lee (Rosaceae) 1. With respect to these culture products, pH values, acidities, and viable cell counts were measured, and tastes were evaluated in the same manner as Example 1. The results are shown in Table 3.

TABLE 3

| Additives | Amounts of magnesium chloride added (mol/L) | pH values of culture products | Acidities of culture products | Viable cell counts of culture products (cfu/mL) | Taste |
|---|---|---|---|---|---|
| None | 0 | 5.40 | 3.7 | $8.3 \times 10^8$ | 5 |
| Essence of *Rubus suavissimus* S. Lee | 0.01 | 5.04 | 4.4 | $2.2 \times 10^9$ | 5 |

TABLE 3-continued

| Additives | Amounts of magnesium chloride added (mol/L) | pH values of culture products | Acidities of culture products | Viable cell counts of culture products (cfu/mL) | Taste |
|---|---|---|---|---|---|
| (Rosaceae) 6 Essence of Rubus suavissimus S. Lee (Rosaceae) 7 | 0.02 | 4.72 | 6.8 | $5.7 \times 10^9$ | 5 |
| Essence of Rubus suavissimus S. Lee (Rosaceae) 1 | 0.05 | 4.40 | 8.1 | $6.3 \times 10^9$ | 5 |
| Essence of Rubus suavissimus S. Lee (Rosaceae) 8 | 0.1 | 4.31 | 8.5 | $6.6 \times 10^9$ | 5 |
| Essence of Rubus suavissimus S. Lee (Rosaceae) 9 | 0.2 | 4.30 | 8.5 | $7.0 \times 10^9$ | 5 |
| Essence of Rubus suavissimus S. Lee (Rosaceae) 10 | 0.5 | 4.30 | 8.6 | $6.4 \times 10^9$ | 4 |

As is clear from Table 3, it was recognized that use of essences of Rubus suavissimus S. Lee (Rosaceae) which were concentrates obtained through the electrodialysis of extracts of Rubus suavissimus S. Lee (Rosaceae) in which magnesium chloride had been added, particularly essences of Rubus suavissimus S. Lee (Rosaceae) in which 0.02% or more of magnesium chloride had been added, had a tendency to bring about significant growth-promoting effects against lactic acid bacteria. Additionally, it was recognized that, even when magnesium chloride was added to the extract of Rubus suavissimus S. Lee (Rosaceae), the taste was not affected as long as the amount of magnesium chloride was 0.2% or less.

Example 4

Production of Culture Products (4)

Culture products (initial bacterial counts: $1.5 \times 10^6$ cfu/mL) were obtained in the same manner as Example 1 except that the amount of Essence of Rubus suavissimus S. Lee (Rosaceae) 1 added was changed to 0.01%, 0.02%, 0.05%, 0.1%, and 0.5%, respectively. With respect to these culture products, pH values, acidities, and viable cell counts were measured, and tastes were evaluated in the same manner as Example 2. The results are shown in Table 4. Culture medium 5 in Table 4 is identical to the culture medium of Example 1 to which Essence of Rubus suavissimus S. Lee (Rosaceae) 1 was added.

TABLE 4

| Additives | Amounts of Essence of Rubus suavissimus S. Lee (Rosaceae) 1 added (%) | pH values of culture products | Acidities of culture products | Viable cell counts of culture products (cfu/mL) | Taste |
|---|---|---|---|---|---|
| Base medium | 0 | 5.40 | 3.7 | $8.3 \times 10^8$ | 5 |
| Culture medium 1 | 0.01 | 4.75 | 6.2 | $4.9 \times 10^9$ | 5 |
| Culture medium 2 | 0.02 | 4.45 | 7.8 | $6.0 \times 10^9$ | 5 |
| Culture medium 3 | 0.05 | 4.40 | 8.0 | $5.8 \times 10^9$ | 5 |
| Culture medium 4 | 0.1 | 4.39 | 8.1 | $6.4 \times 10^9$ | 5 |
| Culture medium 5 | 0.2 | 4.40 | 8.1 | $6.3 \times 10^9$ | 5 |
| Culture medium 6 | 0.5 | 4.40 | 8.2 | $6.9 \times 10^9$ | 4 |

As is clear from Table 4, it was recognized that growth-promoting effects against lactic acid bacteria were provided by addition of the essence of *Rubus suavissimus* S. Lee (Rosaceae) while tastes of dairy products were little affected. In particular, it was revealed that higher viable cell counts and better tastes were obtained by addition of 0.02% to 0.2% of the essence of *Rubus suavissimus* S. Lee (Rosaceae).

Example 5

Production of Culture Products (5)

By using *Lactobacillus casei* (YIT9029) or *Lactobacillus gasseri* (YIT0192) as the lactic acid bacterium and by using the base medium and the culture medium (culture medium 5) containing 0.2% of the essence of *Rubus suavissimus* S. Lee (Rosaceae), culture products (initial bacterial count: $1.5 \times 10^6$ cfu/mL for *Lactobacillus casei* and $4.5 \times 10^5$ cfu/mL for *Lactobacillus gasseri*) were obtained in the same manner as Example 1. With respect to these culture products, pH values, acidities, and viable cell counts were measured, and tastes were evaluated in the same manner as Example 1. The results are shown in Table 5.

TABLE 5

|  | Base medium | | | Culture medium 5 | | |
| --- | --- | --- | --- | --- | --- | --- |
|  | Acidity | pH | Viable cell counts of culture products (cfu/mL) | Acidity | pH | Viable cell counts of culture products (cfu/mL) |
| *Lactobacillus casei* | 3.7 | 5.40 | $8.3 \times 10^8$ | 8.1 | 4.40 | $6.3 \times 10^9$ |
| *Lactobacillus gasseri* | 2.6 | 5.73 | $4.3 \times 10^7$ | 3.8 | 5.34 | $2.4 \times 10^8$ |

As is clear from Table 5, it was recognized that a growth-promoting effect was provided also against a lactic acid bacterium such as *Lactobacillus gasseri* which did not grow well in the base medium, by addition of the essence of *Rubus suavissimus* S. Lee (Rosaceae).

Example 6

Production of a Culture Product (6)

A 15% powdered skim milk solution containing 0.4% of glucose and 3% of fructose was used as a base medium, 0.2% of Essence of *Rubus suavissimus* S. Lee (Rosaceae) 1 prepared in Production Example 1 was added thereto, and the medium was subjected to a heat sterilization at 100° C. for 60 minutes, thereby preparing a culture medium. 0.5% of a starter of *Lactobacillus casei* (YIT9029) was inoculated into the culture medium (the initial bacterial count: $7.6 \times 10^7$ cfu/mL). The inoculated culture medium was incubated at 37° C. until the pH reached 3.7, and then, was cooled to below 10° C., thereby obtaining a culture product. With respect to the culture products, the time required for culturing was measured, and the viable cell count in the culture product was measured in the same manner as Example 1. The results are shown in Table 6.

TABLE 6

| Additive | Time required for culturing (hours) | Viable cell counts in culture products (cfu/mL) | Taste |
| --- | --- | --- | --- |
| None | 90 | $3.2 \times 10^9$ | 5 |
| Essence of *Rubus suavissimus* S. Lee (Rosaceae) 1 | 61 | $6.2 \times 10^9$ | 5 |

As is clear from Table 6, the time required for culturing of *Lactobacillus casei* could be reduced to two thirds by adding the essence of *Rubus suavissimus* S. Lee (Rosaceae) to the culture medium.

Example 7

Production of a Lactic Acid Bacteria Beverage

An aqueous solution containing 30% of glucose-fructose sugar syrup, 25% of hydrogenated starch syrup, 0.3% of vitamin C, 0.3% of soybean polysaccharides and 0.03% of sucralose was sterilized at 100° C. for 10 minutes, 75 parts by weight of the sterilized aqueous solution were added to 25 parts by weight of a mixture obtained by homogenizing the culture product produced in Example 6 at 15 MPa, and then, 0.1% of a yogurt flavor (manufactured by Kabushiki Kaisha Yakult Material) was added to the mixture, thereby producing a lactic acid bacteria beverage. The lactic acid bacteria beverage was packaged in a 65-mL polystyrene container. With respect to the obtained lactic acid bacteria beverage, in the same manner as Example 1, the viable cell count was measured and the taste was evaluated, immediately after the production (immediately after packaging) and after 21 days of storage at 10° C. The results are shown in Table 7. Additionally, the survival rate after 21 days of storage of the lactic acid bacteria beverage at 10° C. was calculated by the following formula.

TABLE 7

|  | Immediately after packaging | | After 21 days of storage at 10° C. | | |
| --- | --- | --- | --- | --- | --- |
| Additive | Viable cell counts (cfu/mL) | Taste | Viable cell counts (cfu/mL) | Taste | Survival rate (%) |
| None | $7.9 \times 10^8$ | 5 | $3.4 \times 10^8$ | 5 | 43 |
| Essence of *Rubus suavissimus* S. Lee (Rosaceae) 1 | $1.6 \times 10^9$ | 5 | $1.0 \times 10^9$ | 5 | 62.5 |

Survival rate (%)=viable cell count after 21 days of storage at 10° C./viable cell count immediately after packaging×100  [Mathematical Formula 1]

As is clear from Table 7, it was shown that, with respect to the lactic acid bacteria beverage prepared with the culture medium containing the essence of *Rubus suavissimus* S. Lee (Rosaceae), a reduction in the viable cell count after storage was suppressed compared with the lactic acid bacteria beverage prepared with the culture medium not containing the essence.

INDUSTRIAL APPLICABILITY

The lactic acid bacteria culture product of the present invention can be used for fermented dairy products and the like which are useful in improving health.

The invention claimed is:

1. A lactic acid bacteria culture product which is obtained by culturing a lactic acid bacterium in a culture medium, wherein the culture medium comprises an essence of *Rubus suavissimus* S. Lee (Rosaceae) which is a concentrate obtained through an electrodialysis of a mixture obtained by adding an inorganic salt to an extract of *Rubus suavissimus* S. Lee (Rosaceae).

2. The lactic acid bacteria culture product according to claim 1, wherein the inorganic salt is at least one selected from a potassium salt, a sodium salt, a calcium salt and a magnesium salt.

3. The lactic acid bacteria culture product according to claim 1, wherein the inorganic salt is a magnesium salt.

4. The lactic acid bacteria culture product according to claim 1, wherein the inorganic salt is present in amount of 0.02 to 0.2 mol/L.

5. A fermented dairy product, comprising the lactic acid bacteria culture product according to claim 1.

6. A method of producing a lactic acid bacteria culture product, the method comprising:
blending an essence of *Rubus suavissimus* S. Lee (Rosaceae) into a culture medium at of the lactic acid bacteria culture product which is obtained by culturing a lactic acid bacterium in the culture medium, wherein the essence of *Rubus suavissimus* S. Lee (Rosaceae) is a concentrate obtained through an electrodialysis of a mixture obtained by adding an inorganic salt to an extract of *Rubus suavissimus* S. Lee (Rosaceae).

7. A method for promoting growth of a lactic acid bacterium, the method comprising:
blending an essence of *Rubus suavissimus* S. Lee (Rosaceae) into a culture medium, wherein the essence of *Rubus suavissimus* S. Lee (Rosaceae) is a concentrate obtained through an electrodialysis of a mixture obtained by adding an inorganic salt to an extract of *Rubus suavissimus* S. Lee (Rosaceae); and
culturing the lactic acid bacterium in the culture medium.

8. The lactic acid bacteria culture product according to claim 3, wherein the inorganic salt is present in an amount of 0.02 to 0.2 mol/L.

9. A fermented dairy product, comprising the lactic acid bacteria culture product according to claim 8.

10. The lactic acid bacteria culture product according to claim 1, wherein the lactic acid bacterium is selected from the group consisting of the genus *Lactobacillus*, the genus *Streptococcus*, the genus *Lactococcus* and the genus *Enterococcus*.

11. The lactic acid bacteria culture product according to claim 1, wherein the lactic acid bacterium is selected from the group consisting *Lactobacillus casei, Lactobacillus gasseri, Lactobacillus acidophilus, Lactobacillus cremoris, Lactobacillus helveticus, Lactobacillus salivarius, Lactobacillus fermentum, Lactobacillus yoghurti, Lactobacillus delbrueckii* subsp. *bulgaricus, Lactobacillus delbrueckii* subsp. *delbrueckii,* and *Lactobacillus johnsonii.*

12. The lactic acid bacteria culture product according to claim 1, wherein the lactic acid bacterium is *Streptococcus thermophiles.*

13. The lactic acid bacteria culture product according to claim 1, wherein the lactic acid bacterium is selected from the group consisting of *Lactococcus lactis* subsp. *lactis, Lactococcus lactis* subsp. *cremoris, Lactococcus plantarum,* and *Lactococcus raffinolactis.*

14. The lactic acid bacteria culture product according to claim 1, wherein the lactic acid bacterium is *Enterococcus faecalis* or *Enterococcus faecium.*

* * * * *